United States Patent [19]

Zetler et al.

[11] 4,351,829
[45] Sep. 28, 1982

[54] USE OF POLYPEPTIDES AS ANALGESIC DRUGS

[75] Inventors: Gerhard Zetler, Lübeck, Fed. Rep. of Germany; Alessandro Rossi, Barzini; Chiara De Paolis, Milan, both of Italy

[73] Assignee: Farmitalia Carlo Erba Spa, Milan, Italy

[21] Appl. No.: 191,146

[22] Filed: Sep. 26, 1980

[51] Int. Cl.³ .................... A61K 37/00; C07C 103/52
[52] U.S. Cl. .............................. 424/177; 260/112.5 R
[58] Field of Search .................. 424/177; 260/112.5 R

[56] References Cited

U.S. PATENT DOCUMENTS

| | | | |
|---|---|---|---|
| 3,472,832 | 10/1969 | Bernardi et al. | 424/177 |
| 3,488,726 | 1/1970 | Ondetti et al. | 424/177 |
| 3,892,726 | 7/1975 | Ondetti et al. | 424/177 |
| 3,937,819 | 2/1976 | Ondetti et al. | 424/177 |

OTHER PUBLICATIONS

Biol. Abstr. 70, 53100.

Primary Examiner—Delbert R. Phillips
Attorney, Agent, or Firm—Brooks, Haidt, Haffner & Delahunty

[57] ABSTRACT

A method of treating pain of whatever origin and nature in human and animal which comprises administering to the patient in need an effective amount of a polypeptide of structure:

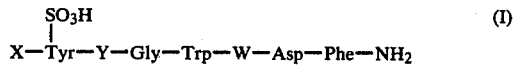

(I)

wherein X is selected from the group consisting of hydrogen, t-butyloxycarbonyl(Boc), Asp, Pyr—Glu, Pyr—Gln—Asp, Pyr—Asn—Asp;
 Y is selected from the group consisting of Thr, Met, Leu, Nle, Val;
 W is selected from the group consisting of Met, Nle, Leu.

4 Claims, No Drawings

USE OF POLYPEPTIDES AS ANALGESIC DRUGS

BACKGROUND OF THE INVENTION

The polypeptides of structure (I) wherein Asp, Pyr-Glu, Pyr-Gln-Asp and so on are abbreviations, very familiar to those skilled in polypeptide chemistry, indicating amino-acid, dipeptide and tripeptide residues, are known in the literature and the various methods of preparation are described in details therein, see for instance German Pat. No. 1,643,504, British Pat. No. 1,523,038, U.S. Pat. No. 3,705,140, U.S. Pat. Nos. 3,723,406; 3,734,946; 3,839,315.

Some of polypeptides of structure (I) are not covered by the above mentioned patents, such as phyllocaerulein, and $Asn^2$, $Leu^5$-caerulein which are described in papers cited hereinbelow:

Phyllocaerulein

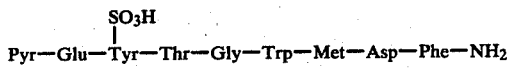

"Structure and pharmacological actions of phyllocaerulein, a caerulein-like nonapeptide: its occurrence in extracts of the skin of phyllomedusa sauvagei and related phyllomedusa species". A. Anastasi, G. Bertaccini, J. M. Cei, G. de Car, V. Erspamer and M. Impicciatore, Brit. J. Pharmacol. 37, 198–206 (1969). "Synthesis of phyllocaerulein", L. Bernardi, G. Bosisio, R. de Castiglione and O. Goffredo, Experientia, 25, 7–8 (1969).

$Asn^2$, $Leu^5$—caerulein

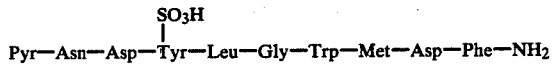

"Occurrence of $Asn^2$, $Leu^5$-caerulein in the skin of the African frog Hylambates maculatus", C. Montecucchi, G. Falconieri, V. Erspamer and J. Visser, Experientia, 33, 1138–1139 (1977).

All these polypeptides possess cholecystokinin activity and are generically active also on the gastro-intestinal tract. One of the most intensively experimented polypeptides of this class is ceruletide, generic name for a decapeptide having the structure:

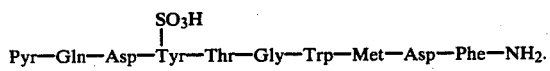

This decapeptide, its chemico-physical, pharmacological properties as well as the detailed preparation are described in U.S. Pat. No. 3,472,832 and in the equivalent foreign patents, among which we quote British Pat. No. 1,146,800 and German Pat. No. 1,643,504 where ceruletide is claimed per se.

Ceruletide is in particular indicated for adjunctive use in cholecystography as it induces contraction of the gallbladder with consequent evacuation of radioopaque bile into the bile ducts.

DESCRIPTION OF THE INVENTION

It was quite unexpectedly found that polypeptides of structure (I)

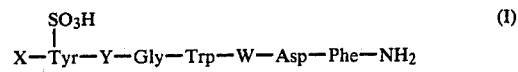

wherein X is selected from the group consisting of hydrogen, t-tubyloxycarbonyl(Boc), Asp, Pyr—Glu, Pyr—Gln—Asp, Pyr—Asn—Asp; Y is selected from the group consisting of Thr, Met, Leu, Nle, Val; W is selected from the group consisting of Met, Nle, Leu, are capable of inducing analgesia both in animals and humans. In fact on the basis of the antagonism exerted by morphin on the gastro-intestinal effects of these polypeptides, it would have to be expected that the pain threshold should be lowered by the administration of these polypeptides. On the contrary, it was surprisingly found that said threshold was remarkably enhanced.

The polypeptides of structure (I) have been proved active as analgesic agents in two experimental situations.

The analgesic effect was assessed by the hot-plate test, slightly modified for the temperature of the heathed plate (53° C.) from Eddy's technique (Eddy, N. B. et al., J. Pharmacol. Exp. Ther., 107: 385, 1953).

To perform this test, the compounds were administered by subcutaneous and intravenous route; they significantly and long lastingly (up to 60 min) delayed the jumping response by the treated mice to the thermal stimulus, starting from the dose of 0.01 mg/Kg body weight.

The analgesic activity of the tested compounds was also confirmed by their inhibiting effect of phenylquinone-or acetic acid-induced writhing.

The method described by Siegmund, E. and Cadmus, R. (Proc. Soc. Exptl. Biol. Med., 95: 729, 1957) was followed. The compounds were administered to mice by subcutaneous and intravenous route and proved active, in a dose-related way, starting from the dose of 0.01 mg/kg (body weight). Tolerance phenomena did not appear over repeated administration. Taking into account that the analgesic activity of the tested compounds in both the above mentioned tests was antagonised by naloxone (a narcotic antagonist) pretreatment at the dose of 0.5 mg/kg by subcutaneous injection, a receptorial assay was performed in order to assess possible affinities of the title compounds for opioid receptors in rat striatal tissue, according to Simantov, R. and Snyder, S. H. (Nature, 262: 505, 1976).

No affinity for dihydromorphine or met-enkephalin receptors was displayed by the tested compounds up to the concentration of $10^{-5}$ M.

These results provisionally stand against a direct opioid-like analgesic activity of the tested compounds.

The addicting liability of the tested compounds (up to the cumulative dose of 2 mg/kg s.c.) was eventually excluded with preliminar challenges versus naloxone in mice, following the jumping-test technique and the observations of the general symptomatology (Huidobro, F. and Maggiolo, M.—Acta Physiol. Latinoam., 11: 201, 1971; Lualdi, P. and Carenzi, A.—Boll. Chim. Farm., 113: 305, 1974).

In order to confirm clinically the analgesic effect, ceruletide has been administered to patients suffering from acute pain due to renal colics and peripheral vascular diseases of the extremities. The results have been quite encouraging.

Moreover, ceruletide has been administered to patients suffering from chronic pain in cancer diseases and from migraine. Also in these cases surprising results in quick complete relief of pain, relief lasting several hours, have been achieved, suggesting that ceruletide can be usefully administered to every patient suffering from severe pain of whatever origin and nature. We quote, among others, pains caused by traumatological accidents, by large burns, by myocardial infarction or angina pectoris.

A further promising clinical employment of the polypeptides of structure (I) may be the use in obstetrical and gynecological field.

The polypeptides of structure (I), comprising ceruletide, may be administered either to humans or to animals in a variety of dosage forms preferably by parenteral route in the form of suitable injectable aqueous solutions.

The polypeptides of structure (I) may be administered as water soluble salts, generally as salts of alkaline metals such as sodium or potassium salts, or alkylamine salts, preferably diethyl-amine salts.

The pharmaceutical or veterinary compositions containing one of the polypeptides of structure (I) and/or salts thereof may be prepared in a conventional way and contain conventional carriers and/or diluents for peptides and salts thereof.

When formulated for injection, polypeptides of structure (I) and salts thereof are preferably presented as sterile powder to be reconstituted with water for injections or other suitable sterile vehicle shortly before administration.

For example, for intravenous or intramusculary injections, sterile aqueous isotonic solutions may be used, preferably sodium chloride isotonic aqueous solution.

The sterile powder is conveniently obtained by means of lyophilization; in that case the active ingredient is conveniently admixed with an inert carrier, such as lactose.

Alternatively, compounds according to the invention may be presented as solutions in aqueous vehicles, and may contain formulatory agents such as stabilizing agents.

The average dosages for Cerulitide were from 0.5 nanograms/kg body weight (i.v.) to 300 nonograms/kg body weight (intramusculary), depending upon the treated pains, as set forth in the following examples.

A clinical essential description regarding No. 47 patients is hereinbelow reported:

Patient 1

M.C.—Age 33 years—Male
Diagnosis:
 Renal colic with hematuria—intense left flank pain.
Treatment:
 Intravenous infusion of Ceruletide administered at the dose of 2 nanograms/kg/min. over 30 minutes in saline solution.
 After 15 minutes from the beginning of the infusion complete relief of pain.

Patient 2

C.A.—Age 40 years—Male
Diagnosis:
 Renal colic with hematuria—intense right flank pain.
Treatment:
 Intravenous infusion of Ceruletide administered at the dose of 2 nanograms/kg/min. over 30 minutes in saline solution.
 After 20 minutes from the beginning of the infusion complete relief of pain.

Patient 3

C.C.—Age 40 years—Male
Diagnosis:
 Renal Colic with hematuria—intense left flank pain.
Treatment:
 Intravenous infusion of Ceruletide at the dose of 2 nonograms/kg/min. over 30 minutes in saline solution.
 After 20 minutes from the beginning of the infusion complete relief of pain.

Patient 4

P.A.—Age 40 years—Male
Diagnosis:
 Renal colic with hematuria—moderate left flank pain.
Treatment:
 Intravenous infusion of Ceruletide at the dose of 2 nanograms/kg/min. over 15 minutes in saline solution.
 After 10 minutes from the beginning of the infusion complete relief of pain.

Patient 5

B.G.—Age 49 years—Male
Diagnosis:
 Renal colic with hematuria—intense left flank pain.
Treatment:
 Intravenous infusion of Ceruletide at the dose of 2 nanograms/kg/min. over 20 minutes in saline solution.
 After 15 minutes from the beginning of the infusion complete relief of pain.

Patient 6

M.G.—Age 41 years—Male
Diagnosis:
 Renal colic with hematuria—intense left flank pain.
Treatment:
 Intravenous infusion of Ceruletide at the dose of 2 nanograms/kg/min. over 10 minutes in saline solution.
 After 5 minutes from the beginning of the infusion complete relief of pain.

Patient 7

D.F.A.—Age 77 years—Male
Diagnosis:
 Gangrene right lower leg with severe pain at rest.
Treatment:
 Intravenous infusion of Ceruletide administered at the dose of 1 nanogram/kg/min. over 2 hours.
 After 15 minutes from the beginning of the infusion complete relief of pain lasting 3 hours, followed by moderate pain for 3 hours.

Patient 8

D.F.D.M.P.—Age 57 years—Male
Diagnosis:
 Femoral obstruction of the left leg with severe pain at rest.
Treatment:
 Intravenous injection in bolus of Ceruletide at the dose of 1 nanogram/kg.

After 15 minutes decrease of pain and complete relief in 30 minutes. The patient remained pain free over 20 hours.

Patient 9

U.F.—Age 57 years—Male
Diagnosis:
Bilateral occlusive vascular disease of the extremities. Sympathectomy. Severe pain at rest.
Treatment:
Intravenous injection in bolus of Ceruletide at the dose of 1 nanogram/kg.
After 20 minutes complete relief of pain.

Patient 10

C.D.—Age 69 years—Male
Diagnosis:
Bilateral femoral obstruction with severe pain at rest.
Treatment:
Intravenous infusion of Ceruletide at dose of 0.5 nanograms/kg/min. over 10 hours.
After 30 minutes relief of pain.

Patient 11

D.M.C.—Age 65 years—Male
Diagnosis:
Gangrene in the right foot with severe pain at rest.
Treatment:
Intravenous injection in bolus of Ceruletide at the dose of 1 nanogram/kg.
After 15 minutes relief of pain.

Patient 12

S.M.—Age 57 years—Male
Diagnosis:
Femoral obstruction of the right leg in diabetic patient with severe pain at rest.
Treatment:
Intravenous infusionn of Ceruletide at the dose of 0.5 nanograms/kg/min. over 10 hours.
Decrease of pain during the whole duration of the infusion.

Patient 13

P.O.—Age 53 years—Male
Diagnosis:
Advanced lung cancer—chronic severe chest pain.
Treatment:
Intravenous injection in bolus of Ceruletide at the dose of 1 nanogram/kg.
After 10 minutes complete relief of pain lasting 10 hours.
Side-effects: None.

Patient 14

I.L.—Age 53 years—Male
Diagnosis:
Lung cancer with bone metastasis—chronic severe chest pain.
Treatment:
Intravenous injection in bolus of Ceruletide at the dose of 1 nanogram/kg.
After 5 minutes complete relief of pain lasting 12 hours.
Side-effects: None.

Patient 15

M.M.—Age 68 years—Female
Diagnosis:
Neoplastic pleuritis after mastectomy with costal and pelvic bilateral metastasis—chronic severe hip and chest pain.
Treatment:
Intravenous injection in bolus of Ceruletide at the dose of 1 nanogram/kg.
After 10 minutes complete relief of pain lasting 6 hours.
Side-effects: None.

Patient 16

G.M.—Age 58 years—Male
Diagnosis:
Adenocarcinoma of the lung—chronic severe chest pain.
Treatment:
Intravenous injection in bolus of Ceruletide at the dose of 1 nanogram/kg.
After 10 minutes complete relief of pain lasting 7 hours.
Side-effects: None.

Patient 17

R.M.—Age 60 years—Male
Diagnosis:
Pancoast's syndrome in lung cancer patient—shoulder and arm chronic intensive pain with severe functional movement limitation of the left arm.
Treatment:
Intravenous injection in bolus of Ceruletide at the dose of 1 nanogram/kg.
After 5 minutes almost complete relief of pain lasting 5 hours with complete dissappearance of the functional movement limitation.
Side-effects: None.

Patient 18

G.P.—Age 56 years—Male
Diagnosis:
Lung cancer with bone metastasis—chronic chest pain.
Treatment:
Intravenous injection in bolus of Ceruletide at the dose of 1 nanogram/kg.
After 15 minutes complete relief of pain lasting 7 hours.
Side-effects: None.

Patient 19

G.G.—Age 62 years—Male
Diagnosis:
Bronchogenic carcinoma—chronic intensive shoulder and chest pain with severe functional movement limitation of the right arm.
Treatment:
Intravenous injection in bolus of Ceruletide at the dose of 1 nanogram/kg.
After 15 minutes complete relief of pain lasting 12 hours. Almost complete disappearance of functional movement limitation.
Side-effects: None.

Patient 20

P.T.—Age 56 years—Male
Diagnosis: Pleural mesothelioma - chronic severe chest pain.
Treatment:
Intravenous injection in bolus of Ceruletide at the dose of 1 nanogram/kg.
After 10 minutes complete relief of pain lasting 7 hours.
Side-effects: None.

Patient 21

F.S.—Age 52 years—Male
Diagnosis: Metastasis from adenocarcinoma - site unknown - chronic severe chest and bone pain.
Treatment:
Intravenous injection in bolus of Ceruletide at the dose of 1 nanogram/kg.
After 10 minutes complete relief of pain lasting 8 hours.
Side-effects: None.

Patient 22

C.R.—Age 73 years—Male
Diagnosis: Lung cancer with bone metastasis - chronic severe bone pain refractory to conventional analgesic treatment.
Treatment:
Intravenous injection in bolus of Ceruletide at the dose of 1 nanogram/kg.
After 10 minutes complete relief of pain lasting 8 hours.
Side-effects: None.

Patient 23

P.E.—Age 38 years—Male
Diagnosis: Lung cancer (?)—chronic severe chest pain.
Treatment:
Intravenous injection in bolus of Ceruletide at the dose of 1 nanogram/kg.
After 10 minutes complete relief of pain lasting 6 hours.
Side-effects: None.

Patient 24

A.P.—Age 62 years—Female
Diagnosis: Neoplastic pleuritis after mastectomy—chronic severe chest pain.
Treatment:
Intravenous injection in bolus of Ceruletide at the dose of 1 nanogram/kg.
After 10 minutes complete relief of pain lasting 12 hours.
Side-effects: None.

Patient 25

M.E.—Age 60 years—Male
Diagnosis: Lung cancer - chronic severe chest pain.
Treatment:
Inravenous injection in bolus of Ceruletide at the dose of 1 nanogram/kg.
After 10 minutes complete relief of pain lasting 8 hours.
Side-effects: None.

Patient 26

M.W.—Age 66 years—Male
Diagnosis: Lung cancer—chronic severe chest pain refractory to conventional analgesic treatments.
Treatment:
Intravenous injection in bolus of Ceruletide at the dose of 1 nanogram/kg.
After 10 minutes complete relief of pain lasting 8 hours.
Side effects: None.

Patient 27

A.G.—Age 56 years—Male
Diagnosis: Pleural mesothelioma - chronic chest and right arm pain.
Treatment:
Intravenous injection in bolus of Ceruletide at the dose of 1 nanogram/kg.
After 15 minutes almost complete and after 30 minutes complete relief of pain lasting 24 hours.
Side-effects: None.

Patient 28

E.D.—Age 18 years—Male
Diagnosis: Meniscus lesion.
Surgery: Exploratory arthrotomy. Burning pain at the surgical operation site.
Treatment:
Intramuscular injection of Ceruletide at the dose of 0.05 micrograms/kg. It is noted that 1 microgram==1,000 nanograms.
After 45 minutes almost complete and after 3 hours complete relief of pain lasting 6 hours.
Side-effects: None.

Patient 29

S.G.—Age 26 years—Male
Diagnosis: Left shin fracture and dislocation.
Surgery: Osteosynthesis devices removal. Pain at the surgical operation site.
Treatment:
Intramuscular injection of Ceruletide at the dose of 0.05 micrograms/kg.
After 30 minutes almost complete and after 1 hour complete relief of pain lasting 8 hours.
Side effects: None.

Patient 30

A.G.—Age 44 year—Male
Diagnosis: Left thigh bone fracture.
Surgery: Osteosynthesis devices removal. Intensive left thigh pain.
Treatment:
Intramuscular injection of Ceruletide at the dose of 0.05 micrograms/kg.
After 1 hour complete relief of pain lasting 5.5 hours.
Side-effects: None.

Patient 31

A.A.—Age 60 year—Male
Diagnosis: Left knee chondromatosis.
Surgery: Arthrotomy. Severe left knee and leg pain.
Treatment:
Intramuscular injection of Ceruletide at the dose of 0.05 micrograms/kg.
After 1 hour almost complete relief of pain lasting 5 hours.
Side-effects: None.

Patient 32

F.C.—Age 14 years—Male
Diagnosis: Left forearm fracture.
Surgery: Osteosynthesis. Intensive forearm pain.
Treatment:
    Intramuscular injection of Ceruletide at the dose of 0.05 micrograms/kg.
    After 45 minutes almost complete relief of pain lasting 5 hours.
Side-effects: None.

Patient 33

C.A.—Age 56 years—Male
Diagnosis: Right epitrochlea hematoma after surgical operation.
Surgery: Hematoma depletion. Intensive pain and burning sensation at the surgical operation site.
Treatment:
    Intramuscular injection of Ceruletide at the dose of 0.05 micrograms/kg.
    After 1 hour almost complete relief of pain lasting 4 hours.
Side-effects: None.

Patient 34

A.A.—Age 20 years—Male
Diagnosis: Penetrating wound of the left knee.
Surgery: Meniscus abscission and tenorrhaphy. Intensive pain and burning sensation at the surgical operation site.
Treatment:
    Intramuscular injection of Ceruletide at the dose of 0.05 micrograms/kg.
    After 2 hours almost complete and after 3 hours complete relief of pain lasting 5.5 hours.
Side-effects: None.
    After the cessation of the analgesic effect, the patient received a second intramuscular injection of Ceruletide at the dose of 0.05 micrograms/kg.
    After 45 minutes almost complete and after 1 hour complete relief of pain lasting 5 hours.
Side-effects: None.

Patient 35

B.G.—Age 44 years—Male
Diagnosis: Right clavicle fracture.
Surgery: Osteosynthesis. Intensive pain at the surgical operation site.
Treatment:
    Intramuscular injection of Ceruletide at the dose of 0.05 micrograms/kg.
    After 45 minutes almost complete and after 1 hour complete relief of pain lasting 7 hours.
Side-effects: None.

Patient 36

S.C.—Age 42 years—Male
Diagnosis: Left knee meniscus lesion.
Surgery: Meniscus abscission. Intensive knee pain.
Treatment:
    Intramuscular injection of Ceruletide at the dose of 0.05 micrograms/kg.
    After 1 hour almost complete and after 2 hours complete relief of pain lasting 6 hours.
Side-effects: None.

Patient 37

S.P.—Age 26 years—Male
Diagnosis: Right clavicle fracture.
Surgery: Osteosynthesis by Kirschner's apparatus. Intensive pain at the surgical operation site.
Treatment:
    Intramuscular injection of Ceruletide at the dose of 0.05 micrograms/kg.
    After 1 hour almost complete and after 2 hours complete relief of pain lasting 4.5 hours.
Side-effects: None.

Patient 38

G.A.—Age 72 years—Female
Diagnosis: Left trochanter fracture.
Surgery: Osteosynthesis. Intensive pain at the surgical operation site.
Treatment:
    Intramuscular injection of Ceruletide at the dose of 0.05 micrograms/kg.
    After 1 hour almost complete relief of pain lasting 4 hours.
Side-effects: None.

Patient 39

D.G.—Age 31 years—Male
Diagnosis: Subcutaneous Achille's tendon rupture.
Surgery: Tenorrhaphy. Heel pain.
Treatment:
    Intramuscular injection of Ceruletide at the dose of 0.05 micrograms/kg.
    After 1 hour almost complete relief of pain lasting 6 hours.
Side-effects: None.

Patient 40

G.O.—Age 45 years—Male
Diagnosis: Left knee meniscus lesion.
Surgery: Meniscus abscission. Intensive pain at the surgical operation site.
Treatment:
    Intramuscular injection of Ceruletide at the dose of 0.05 micrograms/kg.
    After 45 minutes almost complete and after 3 hours complete relief of pain lasting 6 hours.
Side-effects: None.
    After the cessation of the analgesic effect, the patient received a second intramuscular treatment of Ceruletide at the dose of 0.05 micrograms/kg.
    After 45 minutes almost complete and after 2 hours complete relief of pain lasting 6 hours.
Side-effects: None.

Patient 41

B.B.—Age 38 years—Male
Diagnosis: Right knee meniscus lesion.
Surgery: Meniscus abscission. Intensive pain at the surgical operation site.
Treatment:
    Intramuscular injection of Ceruletide at the dose of 0.1 micrograms/kg.
    After 2 hours almost complete and after 3 hours complete relief of pain lasting 6 hours.
Side-effects: None.

Patient 42

P.L.—Age 63 years—Male

Diagnosis: Right clavicle fracture.
Surgery: Osteosynthesis. Burning pain at the surgical operation site.
Treatment:
   Intramuscular injection of Ceruletide at the dose of 0.1 micrograms/kg.
   After 45 minutes almost complete and after 1 hour complete relief of pain lasting 6 hours.
Side-effects: None.

Patient 43

C.M.—Age 15 years—Female
Diagnosis: Left thigh bone fracture.
Surgery: Osteosynthesis. Pain at the surgical operation site.
Treatment:
   Intramuscular injection of Ceruletide at the dose of 0.1 micrograms/kg.
   After 45 minutes almost complete and after 1 hour complete relief of pain lasting 3 hours.
Side-effects: Burning sensation at the injection site.

Patient 44

R.N.—Age 53 years—Female
Diagnosis: Loss of tissue from the left knee.
Surgery: Dermatoplasty. Pain and burning sensation at the wound site.
Treatment:
   Intramuscular injection of Ceruletide at the dose of 0.1 micrograms/kg.
   After 45 minutes almost complete and after 1 hour complete relief of pain lasting 5 hours.
Side-effects: pain sensation at the injection site.

Patient 45

B.M.—Age 23 years—Male
Diagnosis: Left scaphoid bone fracture.
Surgery: Osteosynthesis. Pain at the surgical operation site.
Treatment:
   Intramuscular injection of Ceruletide at the dose of 0.1 micrograms/kg.
   After 45 minutes almost complete and after 2 hours complete relief of pain lasting 3 hours.
Side-effects: None.

Patient 46

Z.G.—Age 32 years—Male
Diagnosis: Right scaphoid bone fracture.
Surgery: Osteosynthesis. Wrist pain.
Treatment:
   Intramuscular injection of Ceruletide at the dose of 0.1 micrograms/kg.
   After 45 minutes almost complete and after 1 hour complete relief of pain lasting 10 hours.
Side-effects: Burning sensation at the injection site.

Patient 47

D.S.C—Age 25 years—Male
Diagnosis: Clavicle fracture.
Surgery: Osteosynthesis. Pain at the surgical operation site.
Treatment:
   Intramuscular injection of Ceruletide at the dose of 0.1 micrograms/kg.
   After 45 minutes almost complete and after 1 hour complete relief of pain lasting 8 hours.
Side-effects: Burning sensation at the injection site.

Polypeptides comprised in the general formula I which are of special importance and thus preferred embodiments in the method of inducing analgesia according to the present invention are as below:

$$\text{Pyr—Gln—Asp—Tyr(SO}_3\text{H)—Thr—Gly—Trp—Met—Asp—Phe—NH}_2 \quad (1)$$
(ceruletide) (X = Pyr—Gln—Asp, Y = Thr, W = Met)

$$\text{Pyr—Gln—Asp—Tyr(SO}_3\text{H)—Thr—Gly—Trp—Nle—Asp—Phe—NH}_2 \quad (2)$$
(X = Pyr—Gln—Asp, Y = Thr, W = Nle)

$$\text{Pyr—Gln—Asp—Tyr(SO}_3\text{H)—Val—Gly—Trp—Nle—Asp—Phe—NH}_2 \quad (3)$$
(X = Pyr—Gln—Asp, Y = Val, W = Nle)

$$\text{Asp—Tyr(SO}_3\text{H)—Met—Gly—Trp—Met—Asp—Phe—Nh}_2 \text{ (CCK-8)} \quad (4)$$
(X = Asp, Y = Met, W = Met)

$$\text{Boc—Tyr(SO}_3\text{H)—Thr—Gly—Trp—Leu—Asp—Phe—NH}_2 \quad (5)$$
(X = Boc, Y = Thr, W = Leu)

$$\text{Boc—Tyr(SO}_3\text{H)—Thr—Gly—Trp—Nle—Asp—Phe—NH}_2 \quad (6)$$
(X = Boc, Y = Thr, W = Nle)

$$\text{H—Tyr(SO}_3\text{H)—Thr—Gly—Trp—Nle—Asp—Phe—NH}_2 \quad (7)$$
(X = H, Y = Thr, W = Nle)

We claim:
1. A method of inducing analgesia in animal and human patients suffering from severe pains selected from biliary and renal colic pains, pains caused by peripheral vascular diseases of the extremities, migraine chronic pains in cancer diseases, post-operatory-, traumatological-, large burns-, myocardial infarction- and angina pectoris pains, which comprises administering to the patient in need an effective amount of a polypeptide selected from ceruletide and salts thereof.
2. A method in accordance with claim 1 wherein the polypeptide is administered by parenteral route.
3. A method in accordance with claim 2, wherein the polypeptide used is Ceruletide and salts thereof.
4. A method in accordance with claim 3, wherein Ceruletide is administered to the patient in need at a dose level of from 0.5 nanograms/kg body weight (i.v.) to 300 nanograms/kg body weight (intramusculary) in admixture with the usual carriers suitable for the parenteral administration.

* * * * *